April 16, 1957 R. BAERMAN ET AL Plant Pat. 1,591
GLADIOLUS PLANT
Filed Feb. 10, 1956
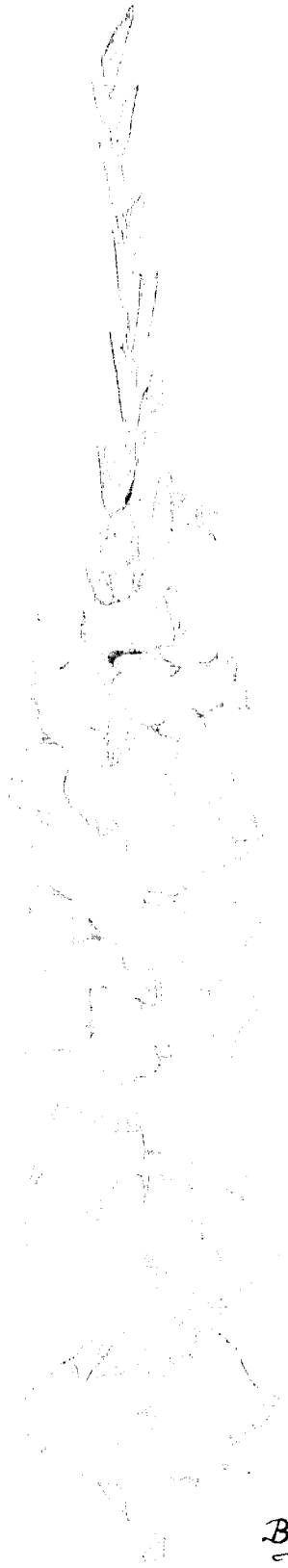
INVENTORS
RALPH BAERMAN and
CARL H. FISCHER
By Lamont Johnston
ATTORNEY United States Patent Office Plant Pat. 1,591

Patented Apr. 16, 1957

1,591

GLADIOLUS PLANT

Ralph Baerman, St. Charles, Minn., and Carl H. Fischer, Arlington, Va., assignors to Selected Glads, Inc., Nashville, Tenn., a corporation of Tennessee Application February 10, 1956, Serial No. 564,838

1 Claim. (Cl. 47—60)

Our present invention relates to a new and improved variety of gladiolus plant and is notable particularly for size and quantity of bloom, vigorous growth, disease resistance, and distinctive color combination.

This variety is the result of a cross between the varieties Beauty's Blush as the seed parent and Friendship as the pollen parent (both unpatented). Hand pollination was accomplished by the first-named inventor in a rented garden near his home when living at Suitland, Maryland. Asexual reproduction in Minnesota by the second-named inventor, by natural increase from cormels through several generations, has shown its characteristics to be permanent.

The accompanying illustration shows a single spike of the bloom of this new variety in approximately its true colors.

Color plate references in the following detailed description indicate Ridgeway's Color Standards and Nomenclature, edition 1912. Where there are other references to color, the ordinary dictionary meaning of the term is intended.

*The plant*

Growth habits: Very vigorous, averaging 60 inches in height under good growing conditions. Is a very good propagator.

Blooming habit: Each spike opens 7 to 9 of its large flowers at one time on spikes totalling 20 to 22 flowers and buds. The variety is an early-midseason bloomer, coming into flower from No. 1 bulbs in 75 to 80 days.

Disease resistance: Very resistant to diseases commonly affecting gladiolus, such as Fusarium wilt, Sclerotinia dry rot, and Botrytis, observed when grown as a seedling under irrigation in a black loam soil in the vicinity of St. Charles, Minnesota, under the natural conditions provided by the climate of that area. At the end of the season, other varieties and seedlings would succumb to the various diseases, whereas this variety remained hale and hearty even when grown alongside varieties that are diseased.

Stems: Straight, wiry and whip-like; approximately Parrot Green (Plate VI). Diameter at base averages 1 to 1¼ inches.

Foliage: Spinach Green (Plate V). Averages 2½ inches wide and 38 inches high.

Corms: Healthy, smooth and with a normal husk. Average size from mature plants is 3 inches in diameter.

*Bloom*

Spike: Long and slender. Has 20 to 22 buds and flowers, of which 3 to 5 open the first day, following which 7 to 9 are open at one time until all have bloomed.

Bud:

*Size.*—Buds beginning to open are 3 inches long.

*Color.*—Light Rose Doree (Pl. 1).

*Opening.*—Seven to 9 buds show color at one time, with 3 to 5 opening the first day.

Flower:

*Arrangement.*—Flowers are closely and evenly spaced on the spike and all face in the same direction.

*Size.*—Lower blooms average 5½ inches across when allowed to bloom in the field. Upper blooms hold their size well, but with a gradual diminution in diameter. Blooms are smaller when cut in the bud stage and brought to bloom indoors.

*Form.*—Wide-open; regular; with six petals, the three upper ones larger than the others.

*General color effect.*—Rose and white.

*Keeping qualities.*—Flowers keep and ship very well.

Petals:

*Shape.*—Upper petals are unusually wide. There is a light ruffling or wrinkling at the extreme edge, extending inward ¼ to ½ inch.

*Size.*—Three upper petals are 2 to 2½ inches wide; lower petals are 1¼ to 1¾ inches wide.

*Aspect.*—Substance is heavy; surface texture smooth and waxy.

*Fragrance.*—None.

*Color.*—Soft yet vivid. The petals are a light Rose Doree (Plate I) at the tips and edges, blending to Geranium Pink (Plate I) as the predominant flower color, with La France Pink (Plate I) in the upper throat. On the lower throat petals—one or two in each flower—there are large white throat blotches comprising more than half the area of the throat petals. A distinct line of white extends into the midrib of each petal, usually to within ½ inch of the tip.

Reproductive organs:

*Stamens.*—Of average size; white, with open side of anthers edged with La France Pink (Plate I).

*Pistils.*—Three-pronged, extending considerably beyond the stamens; white.

*Comparisons*

Our new gladiolus variety resembles the varieties Friendship and Spic and Span (unpatented) more than any other varieties known to us, but differs from them principally as follows:

1. Our variety is taller than Friendship.
2. Our variety has a longer flowerhead than Friendship.
3. Our variety has larger flowers than Friendship.
4. Our variety blooms 10 to 14 days later than Friendship.
5. The florets of our variety have larger and whiter throat blotches than those of Friendship.
6. Our variety has a white throat blotch which is not found in Spic and Span (unpatented), the latter having a Strawberry Pink (Plate I) throat with a few darker pink lines deep in the throat.
7. The prevailing color of the flower of our variety is Geranium Pink (Plate I), blending to Rose Doree (Plate I) at the tips and to La France Pink (Plate I) in the upper throat, whereas Spic and Span is Peach Red (Plate I) and Strawberry Pink (Plate I).
8. Our variety has fewer buds showing color at one time than is true of Spic and Span.

Having thus disclosed our invention, we claim:

The new and distinct variety of gladiolus plant with novel combination of features, substantially as herein shown and described, characterized particularly by its vigorous growth and resistance to disease; its long and slender spike; the regular and compact arrangement of its flowers on its spikes, with all facing in the same direction; its large, healthy corms; and the many large, lightly-ruffled flowers, with excellent keeping qualities and distinctive vivid coloring as indicated.

No references cited.